(12) United States Patent
Hall et al.

(10) Patent No.: US 6,359,212 B1
(45) Date of Patent: *Mar. 19, 2002

(54) METHOD FOR TESTING SOLAR CELL ASSEMBLIES AND SECOND SURFACE MIRRORS BY ULTRAVIOLET REFLECTOMETRY FOR SUSCEPTIBILITY TO ULTRAVIOLET DEGRADATION

(75) Inventors: James T. Hall, Torrance; Frederick D. Cottrell, Redondo Beach, both of CA (US)

(73) Assignee: TRW Inc., Redondo Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/615,385

(22) Filed: Jul. 13, 2000

(51) Int. Cl.$^7$ .................. H01L 31/048; G01N 21/00
(52) U.S. Cl. .............. 136/290; 136/256; 356/239.2; 356/237.2; 324/501; 324/765; 359/838; 359/900
(58) Field of Search .................. 136/290, 256; 356/239.2, 237.2; 324/501, 765; 359/838, 900

(56) References Cited

U.S. PATENT DOCUMENTS

| | | | | |
|---|---|---|---|---|
| 5,334,844 A | * | 8/1994 | Pollard et al. | 136/290 |
| 5,367,174 A | * | 11/1994 | Bazile et al. | 136/290 |
| 6,111,638 A | * | 8/2000 | Chou et al. | 356/239.2 |
| 6,154,034 A | * | 11/2000 | Lovelady et al. | |

* cited by examiner

Primary Examiner—Alan Diamond
(74) Attorney, Agent, or Firm—Connie M. Thousand (57) ABSTRACT

A method for determining the susceptibility of solar cell cover glass or second surface mirror to ultraviolet (UV) degradation comprises the steps of illuminating the solar cell cover glass with ultra violet light at a preselected illumination angle where the solar cell cover glass reflects a portion of the ultraviolet light; measuring the reflected portion of the ultraviolet light; and, characterizing the propensity of the cover glass or contaminate layer on a second surface mirror to degradation as a function of the reflectance. The process results in an improvement of the long-term power output of solar cells by screening out cover glasses that have a propensity to darken under solar-equivalent UV exposure and thus maintaining optical transparency arising from increased solar absorption in darkened cover glass. The process will additionally result in decreased contaminant levels on thermal control surfaces and less on-orbit degradation.

20 Claims, 6 Drawing Sheets

METHOD FOR TESTING SOLAR CELL ASSEMBLIES AND SECOND SURFACE MIRRORS BY ULTRAVIOLET REFLECTOMETRY FOR SUSCEPTIBILITY TO ULTRAVIOLET DEGRADATION

CROSS-REFERENCE TO RELATED APPLICATIONS

This application is related to the following commonly assigned application: "Method for Testing Solar Cell Assemblies by Ultraviolet Laser Irradiation for Susceptibility to Ultraviolet Degradation", application Ser. No. 09/628,196 pending.

BACKGROUND OF THE INVENTION

This invention relates generally to solar cell assemblies and second surface mirrors which are especially useful in space, and more particularly to a method for testing such solar cell assemblies and second surface mirrors to identify those that have a susceptibility to ultraviolet degradation.

Solar panels are conventionally used as a source of electrical power for spacecraft such as satellites. The solar panels typically used for spacecraft include a substrate and a plurality of individual photovoltaic solar cells which are secured to a face surface of the substrate. The individual solar cells are electrically connected together to form a series-parallel solar cell array which, when oriented properly toward the sun, converts solar energy into electrical energy. A cover glass, typically made of a borosilicate material, covers the individual solar cells and together with the cells forms a solar cell assembly.

The efficiency of a solar cell is directly related to the amount of useful light which is absorbed by the solar cell. Only a portion of the light striking the top surface of a solar cell is useful to the cell. Another portion of the light striking the cell is nonuseful, i.e., the light has wavelengths outside the range useful to the cell; and yet another portion of light is reflected by the solar cell. To reduce the problem of light reflection, solar cells employ an antireflective (low reflectance) coating positioned on the surface of the solar cell through which light enters. To reduce solar heating effects, an alternative coating design provides antireflective properties over only the useful range of wavelengths while also highly reflecting non useful wavelengths.

One of the most important consideration for solar assemblies and panels used on spacecraft is efficiency. If a solar panel degrades in space, it is difficult, if not impossible, to correct or compensate for the resulting loss of electrical power with the result that the useful life of the entire spacecraft is often prematurely ended.

Second surface mirrors are fused silica or borosilicate glass with a silver coating on the back side that are used to radiate thermal energy from heat producing components, and reflect incident solar radiation. Solar energy passes through the fused silica and is reflected from the silver surface to prevent excessive heating when exposed to the sun. Efficiency can be seriously degraded by very small amounts of surface contamination that absorb energy on the mirrors surface. Layers of contaminants as little as 300 Angstroms thick will darken when exposed to the space environment and result in a serious increase in the solar absorptance of the second surface mirrors. This will result in increased heating of the mirrors when exposed to sunlight and potential degradation of the spacecraft performance due to excessive heating.

In the deployed configuration, the solar panels are subjected to substantial thermal stresses; the solar cells and the front surfaces of the substrates and cover glasses are subjected to the intense heat of the sun while the back surfaces of the substrates are subjected to the extreme cold of outer space. Furthermore, the cover glasses may be susceptible to degradation (visible darkening) upon exposure to ultraviolet radiation and other radiation in the space environment. Some degradation is expected to lead to a nominal, end-of-life, loss in performance. Abnormal degradation however may be caused by deleterious defects such as impurities and/or contamination sites present in the cover glass and coatings. These defects can absorb radiation at a particular ultraviolet wavelength or wavelengths and can result in visible darkening. This darkening of the cover glass results in less useful light transmitting to the solar cell material, which in turn directly lowers the efficiency and power generated by the solar cell. The darkening may also result in an undesirable increase of the temperature of the assembly arising from the increased solar absorption by the darkened cover glass.

Conventional quality control methods for inspecting solar cell cover glasses examine properties such as trace element levels in the glass substrate and UV reflectance coatings, multilayer coating thickness, and optical quality. These measurements do not necessarily correlate with the propensity of a cover glass to darken on-orbit. In addition, inspectors are not able to inspect cells once the cells are mounted to a solar array. The current inspection methods are susceptible to passing solar cell assemblies that initially meet quality specifications but later degrade upon ultraviolet-induced darkening. In addition, the current inspection methods will not detect contaminant layers which accumulate after the solar cell has been integrated into the array. It thus is desirable to provide a test method that identifies the susceptibility of the solar cell assemblies to on-orbit darkening and degradation and can be practiced on a completed solar array.

Currently, there is no reliable method available to directly measure the amount of surface contamination that is present on second surface mirrors once they are installed on a spacecraft other than visual inspection. The current method used to verify the cleanliness of a second surface mirror includes repeated cleanings and careful protection of the mirrors from contamination sources. This can be costly and requires carefully controlled work areas and elaborate environmental enclosures. In addition, excessive contamination that is left on second surface mirrors and that is not detected has proven to result in overheating and seriously degraded performance. If the cleanliness could be verified prior to launch, the likelihood of degradation can be substantially reduced. As such, better knowledge of the amount of on-orbit degradation would allow the use of less design margin resulting in less radiator area and heater power required for proper spacecraft operation. What is needed therefore is a method that detects cleanliness of a second surface mirror and that can be used close to the launch time of the spacecraft.

SUMMARY OF THE INVENTION

The aforementioned need in the prior art is met by the present invention which provides a method for determining the susceptibility of solar cell cover glass to degradation as well as determining the contamination levels on second surface mirrors. The method comprises the steps of (1) illuminating the solar cell cover glass or second surface mirror with a benign exposure to ultraviolet light at a preselected illumination angle where the solar cell cover glass or the silver layer of the second surface mirror reflects a portion of the ultraviolet light; (2) measuring the reflected portion of the ultraviolet light; and, (3) characterizing the propensity of the cover glass to degradation or characterizing the amount of surface contamination on the second surface mirror as a function of the reflectance.

BRIEF DESCRIPTION OF THE DRAWING

Reference is now made to the Description of the Preferred Embodiment, illustrated in the accompanying drawings, in which.

DESCRIPTION OF THE PREFERRED EMBODIMENT

Figure 1:
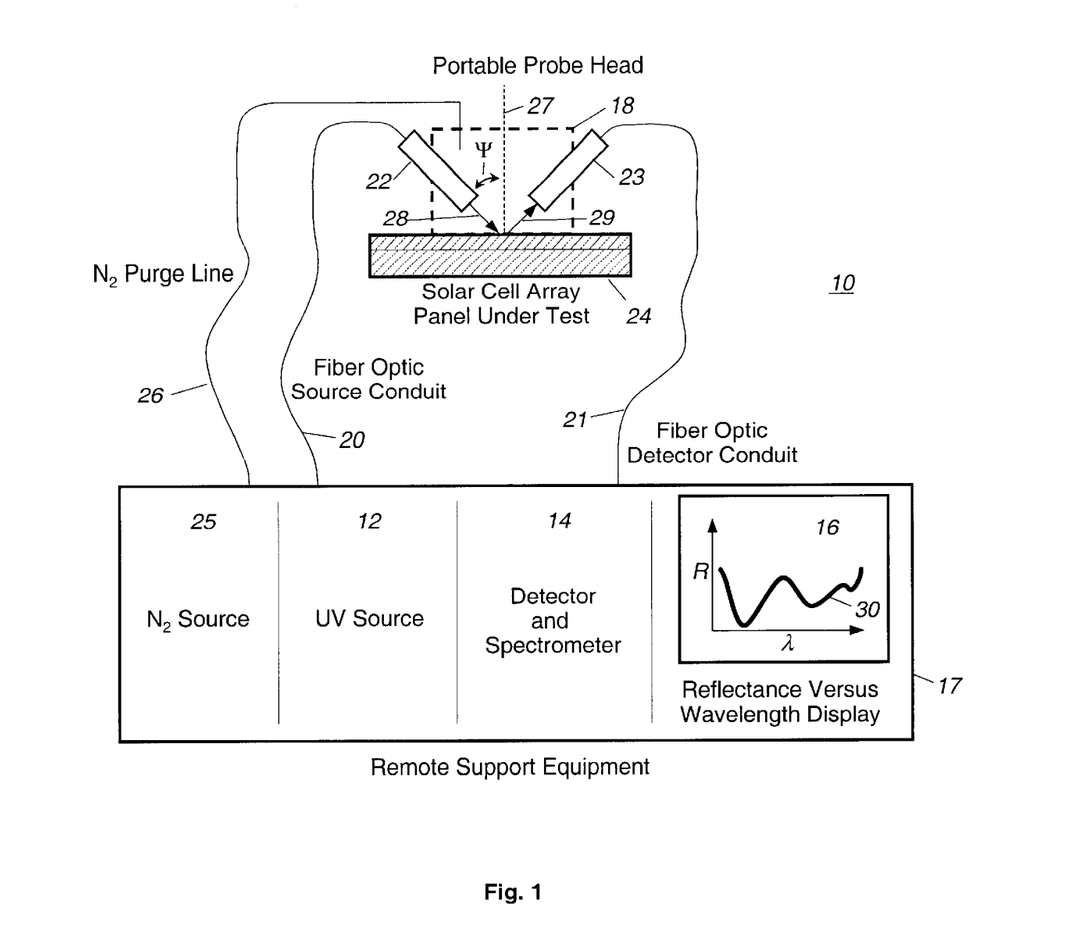
FIG. 1 is a schematic illustration of the apparatus utilized to conduct the testing of the solar cell glass covers for susceptibility to degradation or to test the second surface mirror for surface contamination in accordance with the present invention.

Referring now more particularly to FIG. 1, the method of the present invention is performed using a test apparatus 10 which includes a source of ultraviolet light 12, a monochromation detector and spectrometer 14, and a display 16. The source of ultraviolet light 12 may be any combination of a tungsten halogen lamp, deuterium lamp, xenon lamp, kryton lamp or other source which emits light at ultraviolet wavelengths of between approximately 120 nm and 300 nm. The display 16 would typically be a digital or analog display unit but could also be a computer monitor, though specialized display equipment included with the detector 14 may be utilized.

The ultraviolet source 12 and detector 14 are preferably configured as a part of the remote support equipment 17 and are connected to a portable probe head 18 by fiber optical conduits 20, 21. Focusing optics 22, 23 couple the ultraviolet light between the fiber optic conduits 20, 21 and the solar cell cover glass under test 24. The remote test equipment preferably includes a remote source of compressed nitrogen 25 that is connected to the portable probe head 18 through a nitrogen purge line 26. The nitrogen flushes air out of the probe head housing to avoid ozone production.

The testing of the solar cell cover glass sample 24 occurs as follows. The ultraviolet light source 12 is energized and positioned to illuminate the cover glass 24 at a preselected illumination angle ($\Psi$) which is defined with respect to the normal line 27 of the solar cell cover glass 24. Ultraviolet light, depicted by the line marked 28, is radiated from the ultraviolet light source 12 and impinges upon the surface of the cover glass 24 at the illumination angle ($\Psi$). A portion of the ultraviolet light, depicted by the line marked 29, is reflected by the cover glass 24. The reflected ultraviolet light 29 is sampled and measured by the detector and spectrometer 14. The detector and spectrometer 14 display a graph on the monitor 16 showing a curve 30 of the reflectance versus excitation wavelength for the preselected illumination angle ($\Psi$). The reflectance is a ratio of the reflected ultraviolet light 29 to the incident ultraviolet light 28. As such, the reflectance is a percentage of how much of the incident ultraviolet light 28 is reflected by the cover glass sample 24 for a preselected angle of incidence ($\Psi$).

Figure 2:
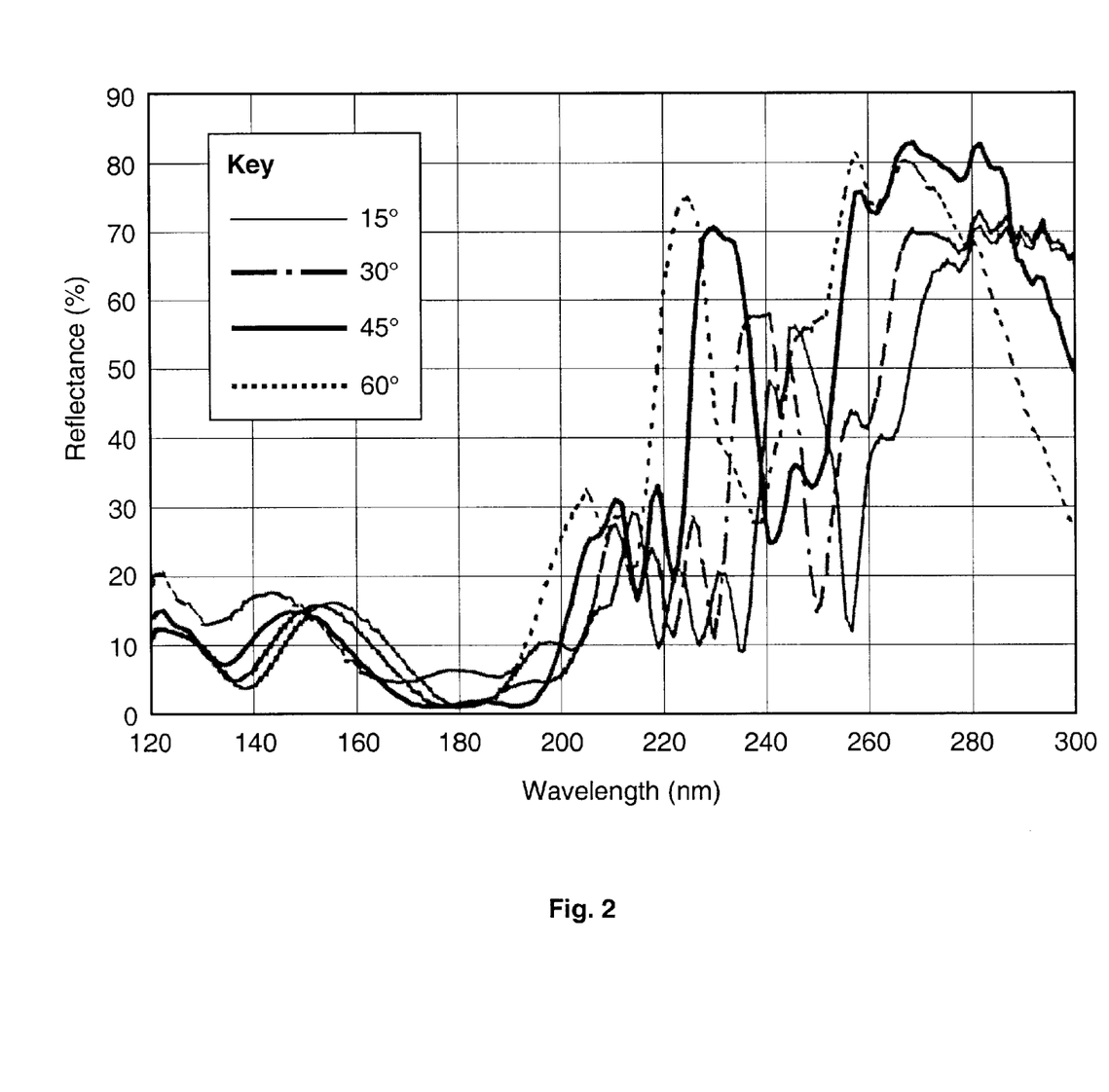
FIG. 2 is a graph illustrating the reflectance of a solar cell cover glass that is susceptible to darkening.

The reflectance measurement is preferably conducted at a plurality of illumination angles ($\Psi$) such that the graph will depict a plurality of curves, one for each illumination angle. For example, the graph of FIG. 2 depicts four curves for a single solar cell cover glass sample where the solid gray curve is for an illumination angle of 15 degrees; the dotted/dashed curve is for an illumination angle of 30 degrees; the solid black curve is for an illumination angle of 45 degrees; and, the dotted curve is for an illumination angle of 60 degrees.

Referring back to FIG. 1, the operator of the testing apparatus 10 reviews the curve 29 to determine whether or not the cover glass sample 24 exhibits either an existing darkening caused by ultraviolet light, such as might be caused in pre-launch ground tests, or has a propensity to darken when inserted on-orbit. To make this determination, the operator must use a propensity-to-darken/not-a-propensity to darken criteria which is also known as a pass/fail criteria.

Figure 3:
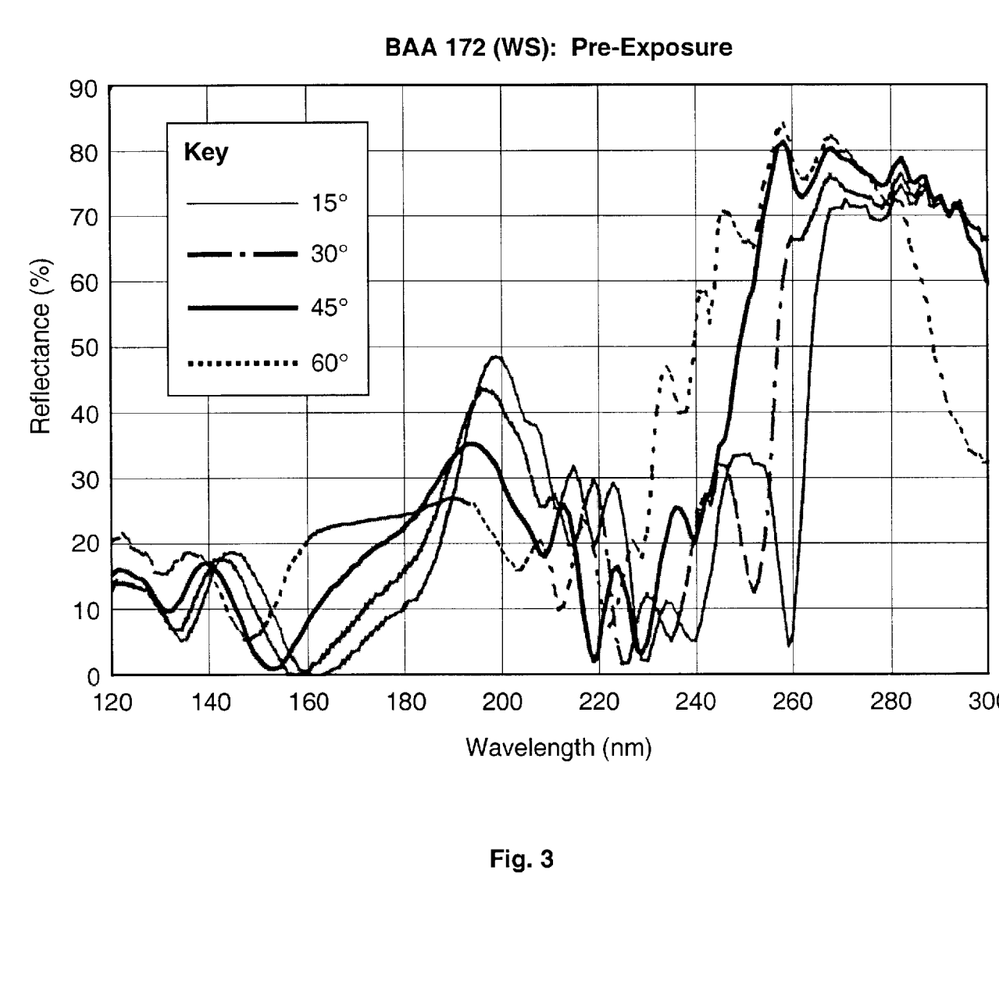
FIG. 3 is a graph illustrating the reflectance of a solar cell cover glass that is not susceptible to darkening.

To establish the pass/fail criteria, reflectance measurements were conducted on cover glass samples which were subsequently exposed to a simulated space environment. The corresponding reflectance graphs were examined for indicia of a propensity to darken after exposure. FIG. 2 depicts a graph of reflectance measurements for a test sample that later abnormally darkened after exposure to the equivalent of approximately one year of solar ultraviolet photons at wavelengths below about 200 nm in a vacuum environment; and, FIG. 3 depicts a graph of reflectance measurements for a test sample which did not darken when exposed to the same environment. The reflectance for the test samples associated with the graphs of FIGS. 2 & 3 was measured for illumination angles of 15, 30, 45 and 60 degrees and are depicted by the gray, dashed/dotted, black and dotted curves respectively. These graphs and curves were used to define the pass/fail criteria.

Many organic contaminates which may adhere to a solar cell cover glass or second surface mirror-have an absorbance at a wavelength band spanning between about 180 and 190 nm. Organic contaminates are known to cause subsequent darkening of the cover glass or second surface mirror upon exposure to ultraviolet radiation in a vacuum environment. A low reflectance over a wide range of incidence angles in the 180–190 nm wavelength indicates that a contaminate is significantly absorbing ultraviolet light. Thus, a cover glass which is likely to darken or second surface mirror sample which has a significant contamination level will exhibit a low reflectance in the 180 to 190 nm wavelength range, particularly persistent at multiple angles of incidence. Comparing the graphs of FIGS. 2 & 3 in the 180–190 nm wavelength for multiple illumination angles of between 15 and 60 degrees the graphs show that the reflectance of a sample which is susceptible to darkening (FIG. 2) is lower than the reflectance of the sample which is not susceptible to darkening (FIG. 3) after exposure to a simulated space environment. As such, if the reflectance is less than about 5% in the 180–190 nm, the sample is categorized as having the propensity-to darken.

Figure 4:
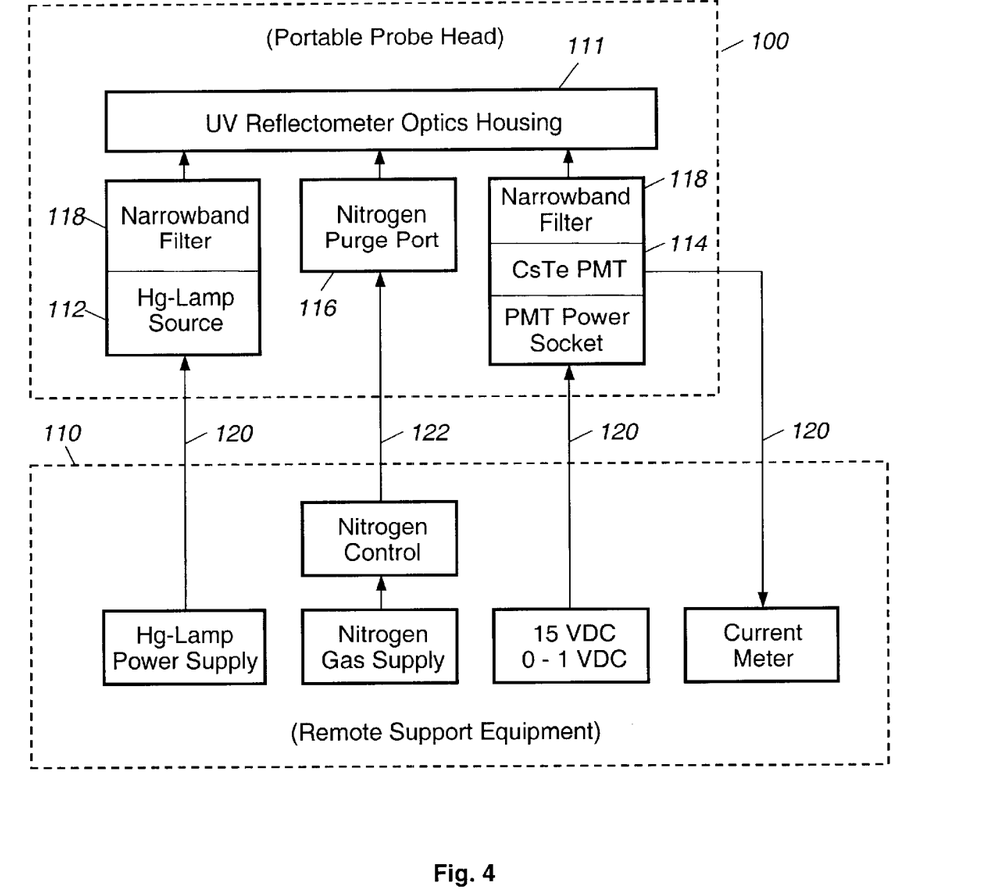
FIG. 4 is a schematic illustration of an apparatus utilized to conduct the testing of the solar cell cover glasses at a selected wavelength and selected angle in accordance with a second embodiment of the invention.
Figure 5:
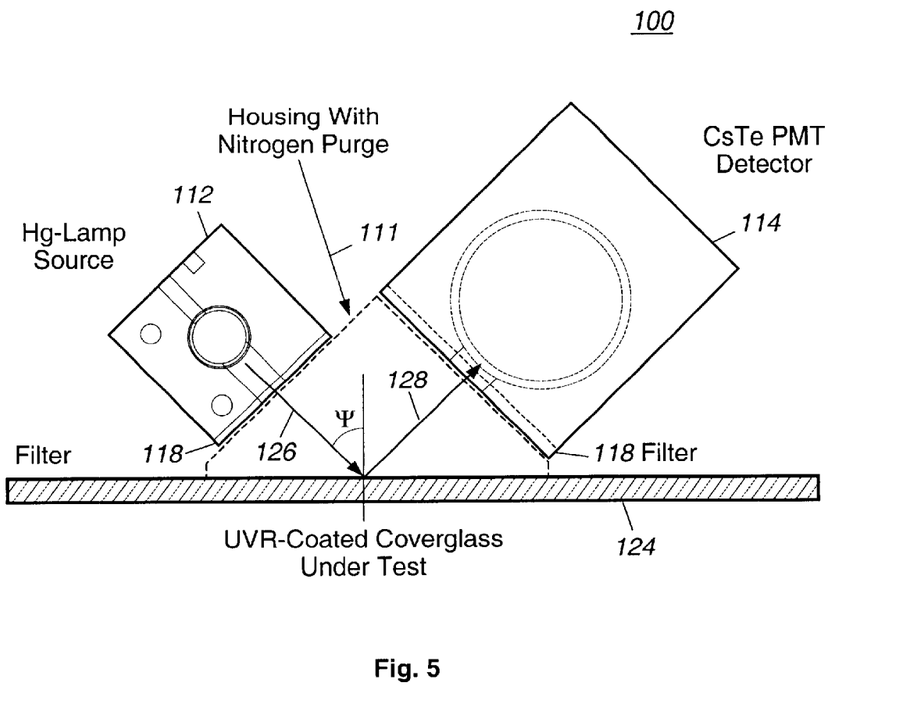
FIG. 5 is an illustration of a cover glass being tested for susceptibility to darkening using the apparatus of FIG. 4 in accordance with the second embodiment of the invention; and, FIG. 6 shows an apparatus useful for spot testing of cover glass in accordance with a third embodiment of the invention.
Figure 6:
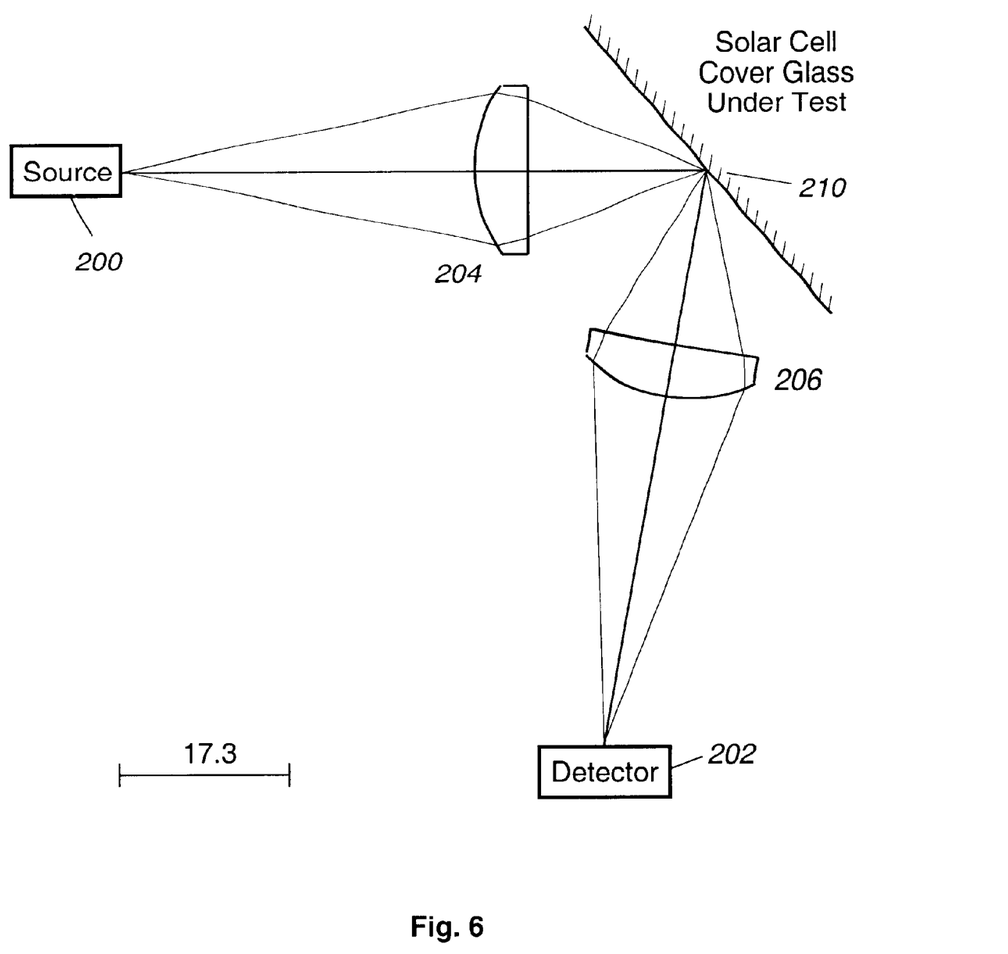

Refer now to FIG. 4 which shows a schematic block diagram of one possible configuration of the portable probe head 100 and the remote support equipment 110; and, FIG. 5 which illustrates the portable probe head design for testing of cover glass using the schematic equipment of FIG. 4. In this embodiment, the portable probe head 100 is encased with a firm but benign (non-damaging) housing 111. The housing 111 is preferably fabricated of a polymer material such as a Delrin™ material fabricated by DuPont corporation. Preferably, black Delrin™ is used for the housing since Delrin™ will not scratch the cover glass under test 124. The probe head 100 comprises a low pressure mercury lamp source 112 configured to operate at a selected, fixed wavelength of about 185 nm. The housing 111 also contains a photomultiplier tube (PMT) detector 114, and a nitrogen purge port 116. One advantage of this embodiment is that no focusing optics are necessary to practice the invention. In series with the source 112 and detectors 114 are narrow-band filters 118 which are used to eliminate essentially all extraneous light except the 185 nm line output of the low-pressure mercury source 112. Electric lines 120 and a nitrogen line 122 connect to the portable probe head 100 and to the remote support equipment 110. A housing 116 is placed over the cover glass under test 124 and is nitrogen purged to remove air from the housing 116. The lamp source 112 is configured to provide ultraviolet light 126 at a 185 nm wavelength. The lamp is positioned to illuminate the cover glass 124 at a preselected Ψ angle, such as an angle of 15, 30, 45 or 60 or any angle therebetween. The detector 114 is positioned to intercept the reflected light 128. To determine if either of the samples associated with the graphs of FIGS. 2 & 3 have the propensity to darken, the operator examines the reflectance of each test sample at a wavelength of 185 nm and at one angle (150, 300 and 45°). A low reflectance, which is defined to be below about 5% would indicate a propensity of the sample to degrade.

FIG. 5 shows an alternative focusing scheme for spot checking small areas and uniformity of the solar cell cover glass coatings. The source 200 and detector 202 focus through lenses 204 and 206 to a spot 210 on a solar cell cover glass under test.

What has been described is an improved process for determining whether or not a solar cell cover glass or a second surface mirror has a propensity for exhibiting degradation, thereby resulting in an improvement of the long-term power output of solar cells by maintaining optical transparency and reducing temperature increases arising from increased solar absorption in darkened cover glasses.

It will be appreciated by persons skilled in the art that the present invention is not limited to what has been shown and described hereinabove. The scope of the invention is limited solely by the claims which follow.

We claim as our invention:

1. A method for determining the susceptibility of solar cell cover glass to degradation, comprising:
   illuminating the solar cell cover glass with ultraviolet light at a wavelength and at an illumination angle where the solar cell cover glass reflects a portion of the ultraviolet light;
   measuring the reflected portion of ultraviolet light; and,
   characterizing the propensity of the solar cell cover glass to degradation as a function of the reflectance and the wavelength.

2. The method of claim 1, wherein characterizing the propensity comprises characterizing the propensity of the solar cell cover glass to degradation as a function of the reflectance at a wavelength between about 180 and 190 nm.

3. The method of claim 2, wherein characterizing comprises determining if the reflectance between the wavelengths of about 180 nm and 190 nm is below about 5%; and, if so, characterizing the solar cell cover glass as having the propensity to darken.

4. The method of claim 3, wherein illuminating the solar cell cover glass comprises illuminating the solar cell cover glass with ultraviolet light at an illumination angle between about 15 and 60 degrees.

5. The method of claim 3, wherein illuminating the solar cell cover glass comprises illuminating the solar cell cover glass with ultraviolet light at a plurality of illumination angles between about 15 and 60 degrees.

6. The method of claim 1, wherein illuminating comprises illuminating the solar cell cover glass with ultraviolet light at about a wavelength of between 180 and 190 nm and at an illumination angle.

7. The method of claim 1, wherein characterizing comprises determining if the reflectance at a wavelength of 185 nm is below about 5%, and, if so, characterizing the solar cell cover glass as having a propensity to darken.

8. The method of claim 1, wherein characterizing comprises comparing at a wavelength of about 185 nm the reflectance of the solar cell cover glass with the reflectance of a first baseline cover glass that has a propensity to darken abnormally and with the reflectance of a second baseline cover glass which is free of propensity to darken abnormally.

9. A method for determining the susceptibility of solar cell cover glass to darkening, comprising:
   illuminating the cover glass with incident ultraviolet light at a wavelength of about 185 nm at an illumination angle where the cover glass reflects a portion of the ultraviolet light;
   measuring the reflected portion of the ultraviolet light at a wavelength of 185 nm; and,
   determining if the reflected portion of the ultraviolet light is less than about 5% of the incident ultraviolet light at the 185 nm wavelength.

10. The method of claim 9, wherein illuminating the cover glass comprises illuminating the cover glass at a fixed illumination angle between 15 and 60 degrees.

11. The method of claim 9, wherein the step of illuminating the solar cell cover glass comprises illuminating the solar cell cover glass with ultraviolet light generated from a mercury lamp having a 185 nm wavelength.

12. The method of claim 9, further comprising detecting the reflected portion of the ultraviolet light with a photomultiplier tube configured to detect radiation at 185 nm.

13. The method of claim 9, further comprising detecting the reflected portion of the ultraviolet light with a photomultiplier tube at 185 nm where said photomultiplier tube is selected from the group consisting of CsTe and CsI photomultiplier tubes.

14. A method for determining the susceptibility of a second surface mirror to degradation, comprising:
   illuminating the second surface mirror with ultraviolet light at a wavelength and at an illumination angle where the second surface mirror reflects a portion of the ultraviolet light;
   measuring the reflected portion of ultraviolet light; and,
   characterizing the propensity of the second surface mirror to degradation as a function of the reflectance and the wavelength.

15. The method of claim 14, wherein characterizing the propensity comprises characterizing the propensity of the second surface mirror to degradation as a function of the reflectance at a wavelength between about 180 and 190 nm.

16. The method of claim 15, wherein characterizing comprises determining if the reflectance between the wavelengths of about 180 nm to 190 nm is below about 5%; and, if so, characterizing the second surface mirror as having the propensity to degrade.

17. The method of claim 16, wherein illuminating the second surface mirror comprises illuminating the second surface mirror with ultraviolet light at an illumination angle between about 15 and 60 degrees.

18. The method of claim 16, wherein illuminating the second surface mirror comprises illuminating the second surface mirror with ultraviolet light at a plurality of illumination angles between about 15 and 60 degrees.

19. The method of claim 14, wherein illuminating comprises illuminating the second surface mirror with ultraviolet light at about a wavelength of between 180 and 190 nm and at an illumination angle.

20. The method of claim 14, wherein characterizing comprises comparing at a wavelength of about 185 nm the reflectance of a second surface mirror with the reflectance of a clean first baseline second surface mirror and with a second baseline second surface mirror having a known significant contamination level.

* * * * *